US008798720B2

(12) United States Patent
Bill et al.

(10) Patent No.: US 8,798,720 B2
(45) Date of Patent: Aug. 5, 2014

(54) METHOD AND DEVICE FOR DETERMINING A POSITION OF A PART OF A MEDICAL INSTRUMENT

(75) Inventors: Ulrich Bill, Effeltrich (DE); Jan Boese, Eckental (DE); James Williams, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 1287 days.

(21) Appl. No.: 12/148,098

(22) Filed: Apr. 16, 2008

(65) Prior Publication Data

US 2008/0285720 A1      Nov. 20, 2008

(30) Foreign Application Priority Data

Apr. 27, 2007    (DE) .......................... 10 2007 020 059

(51) Int. Cl.
*A61B 6/02*      (2006.01)
*A61B 6/00*      (2006.01)
*A61B 6/12*      (2006.01)
*A61B 6/06*      (2006.01)
*A61B 19/00*     (2006.01)

(52) U.S. Cl.
CPC .............. *A61B 6/4035* (2013.01); *A61B 19/54* (2013.01); *A61B 19/52* (2013.01); *A61B 19/201* (2013.01); *A61B 6/12* (2013.01); *A61B 2019/5238* (2013.01); *A61B 6/06* (2013.01); *A61B 6/4441* (2013.01)
USPC ............................ 600/424; 600/407; 378/156

(58) Field of Classification Search
USPC ........................................... 378/156; 600/424
See application file for complete search history.

(56) References Cited

U.S. PATENT DOCUMENTS

| | | | | | |
|---|---|---|---|---|---|
| 4,684,370 | A | * | 8/1987 | Barrett ....................... | 623/16.11 |
| 5,073,910 | A | * | 12/1991 | Eberhard et al. .................. | 378/4 |
| 5,209,725 | A | * | 5/1993 | Roth ............................. | 604/508 |
| 5,751,785 | A | * | 5/1998 | Moorman et al. ............ | 378/146 |
| 6,539,074 | B1 | * | 3/2003 | Yavuz et al. ...................... | 378/4 |
| 6,649,914 | B1 | | 11/2003 | Moorman et al. | |
| 7,130,374 | B1 | * | 10/2006 | Jacobs et al. .................... | 378/76 |
| 2006/0281971 | A1 | * | 12/2006 | Sauer et al. ................... | 600/109 |
| 2008/0157967 | A1 | * | 7/2008 | Jones et al. ................ | 340/572.1 |

FOREIGN PATENT DOCUMENTS

| CA | 2572019 A1 | 1/2006 |
|---|---|---|
| DE | 69318853 T2 | 10/1998 |

* cited by examiner

*Primary Examiner* — Tse Chen
*Assistant Examiner* — Vani Gupta

(57) ABSTRACT

The invention relates to a method and a device for determining the position of a part of a medical instrument with an x-ray sensitive sensor in a plane of an x-ray image using an x-ray facility having an x-ray beam source and a device, which is assigned to the beam source and influences the x-ray radiation emitted by the x-ray beam source, wherein a spatial region, in which the medical instrument is located, is scanned with x-ray radiation and at the same time x-ray radiation is detected with the x-ray-sensitive sensor with the device for influencing the x-ray radiation rotating at constant speed, the rotation being synchronized to the receipt of signals based on x-ray radiation with the x-ray-sensitive sensor and with the position of the part of the medical instrument in the plane of an x-ray image being determined based on the x-ray radiation detected with the x-ray-sensitive sensor.

12 Claims, 4 Drawing Sheets

METHOD AND DEVICE FOR DETERMINING A POSITION OF A PART OF A MEDICAL INSTRUMENT

CROSS REFERENCE TO RELATED APPLICATIONS

This application claims priority of German application No. 10 2007 020 059.7 filed Apr. 27, 2007, which is incorporated by reference herein in its entirety.

FIELD OF THE INVENTION

The invention relates to a method and device for determining the position of at least a part of a medical instrument in a plane of an x-ray image using an x-ray facility.

BACKGROUND OF THE INVENTION

In minimally invasive medical interventions, in which a medical instrument, such as a catheter, stent or biopsy needle, is inserted into the body of a patient and therefore can generally no longer be captured visually by eye directly, it is necessary, for example to navigate the medical instrument in the body of the patient, to overlay an image of at least the relevant part of the instrument on image information from inside the patient's body. A physician carrying out the navigation operation, e.g. an interventional radiologist, a neuroradiologist or a cardiologist, wants to be informed at all times during the navigation operation about the position of the instrument in relation to the respective anatomy of the patient, in order to be able to navigate in the safest and most precise manner possible.

Until now navigation of instruments inserted into a patient's body has frequently taken place using x-ray images, for example using x-ray fluoroscopy images, in which the respective instrument can be seen. Progress in the miniaturization of instruments and the use of new materials for instruments means that said instruments can no longer be identified or can only be identified with difficulty in x-ray images. Changing the x-ray intensity for imaging such medical instruments in x-ray images represents a health risk, specifically during longer medical interventions, in particular for clinic personnel, carrying out interventions on a continuous basis.

One alternative to navigating an instrument using x-ray fluoroscopy images is to use an optical or electromagnetic tracking or location system. When using an optical tracking system for example one or more optical markers or reflectors are arranged specifically at the proximal end of the instrument, which protrudes out of the body, it being possible to capture these using a camera system of the optical tracking system. The specific arrangement of the markers on the medical instrument makes it possible to determine the position of for example the tip of the instrument in the patient's body in relation to a coordinate system assigned to the optical tracking system. The use of an optical tracking system is however generally hereby restricted to rigid medical instruments.

When using an electromagnetic tracking system the use of a number of transmitters allows a number of electromagnetic fields to be generated for example, in which the medical instrument provided with corresponding sensors is moved inside the patient's body. The electrical signals induced in the sensors can also be used in this manner, with a specific arrangement of the sensors on the medical instrument, to determine for example the tip of the medical instrument in a coordinate system assigned to the electromagnetic tracking system.

Both when using an optical tracking system, like the "Polaris" system from Northern Digital Inc., Waterloo, Ontario, Canada, and when using an electromagnetic tracking system, like the "Aurora" system from Northern Digital Inc., Waterloo, Ontario, Canada, for medical applications of the navigation system it is necessary to register the respective coordinate system of the tracking system with an image coordinate system of an x-ray system or another imaging system, in order to be able to overlay an image of at least a part of the medical instrument on image information relating to the patient obtained with the x-ray system or another imaging system, based on the positions of the medical instrument obtained using the tracking system.

U.S. Pat. No. 6,649,914 B1 discloses an imaging system with x-ray scanning, with which the positions of a catheter inserted into a patient's body and provided with an x-ray sensor can be determined in a plane. The imaging system comprises a scanning x-ray beam source, whose x-ray target is only stimulated point by point by an electron beam to emit so-called pencil beams, with the x-ray target being scanned in a specific form with the aid of a scan generator using the electron beam. If x-ray radiation is detected with the x-ray sensor of a catheter, it is possible to determine the x and y positions of the respective catheter in a plane using the scan data from the scan generator.

SUMMARY OF THE INVENTION

The object of the invention is to specify a method and device of the type mentioned in the introduction such that the position of a medical instrument can be determined as simply as possible for medical interventions.

According to the invention this object is achieved by a method for determining the position of at least a part of a medical instrument provided with at least one x-ray-sensitive sensor in a plane of an x-ray image using an x-ray facility having an x-ray beam source and at least one device, which is assigned specifically to the x-ray beam source and influences the x-ray radiation emitted by the x-ray beam source, wherein a spatial region, in which the medical instrument provided with the x-ray-sensitive sensor is located, is scanned preferably periodically with x-ray radiation emitted by the x-ray beam source and influenced by the device and wherein x-ray radiation is detected at the same time with the x-ray-sensitive sensor, with the position of at least the part of the medical instrument in the plane of an x-ray image being determined based on the x-ray radiation detected with the x-ray-sensitive sensor. According to the invention therefore a medical instrument to be navigated for example inside a patient's body is provided with an x-ray-sensitive sensor, which detects x-ray radiation when a spatial region is scanned with x-ray radiation. The scanning of a spatial region with x-ray radiation here means that the entire spatial region is preferably not subjected to x-ray radiation at essentially the same time and in an essentially uniform manner but preferably only a sub-region of the entire spatial region that can be subjected to x-ray radiation in each instance. By subjecting successive and/or merging sub-regions of the spatial region to x-ray radiation in a preferably continuous or step by step manner, the entire spatial region is gradually scanned with x-ray radiation, preferably in a uniform, periodic manner. Scanning can however also mean that the entire spatial region is subjected to x-ray radiation at the same time but is then subjected to x-ray radiation of differing intensity region by region.

The relevant scannable spatial region is preferably defined by the focal point of the x-ray beam source and/or the shutters of the x-ray beam source assigned to the focal point and by the plane of the x-ray image, in other words the detector plane. The relevant spatial region is therefore essentially conical in shape. If the medical instrument is located in the spatial region or if the medical instrument is moved in the spatial region, x-ray radiation of for example different form, period, intensity, duration, etc. is detected with the x-ray-sensitive sensor, depending on how the x-ray radiation is influenced with the device assigned specifically to the x-ray beam source, with the result that due to the known structure of the device for influencing the x-ray radiation and the known temporal profile of the emitted x-ray radiation it is possible to determine the position of at least the part of the medical instrument in the plane of an x-ray image, in other words in the detector plane. By comparing the temporal profile of the emitted x-ray radiation with the temporal pattern of the x-ray radiation detected with the x-ray-sensitive sensor it is therefore possible to calculate and input the location of the sensor and therefore of a part of the instrument in the plane of the x-ray image.

The position of the x-ray-sensitive sensor and therefore of at least the part of the medical instrument in the plane of an x-ray image is preferably determined in polar coordinates with the radius R (radial coordinate) and the angle φ (angle coordinate). The central x-ray beam emitted from the focal point of the x-ray beam source, which strikes approximately in the center of the input screen of the x-ray beam receiver, hereby coincides at least essentially with the z-axis of the polar coordinate system.

The device for influencing the x-ray radiation rotates at constant angular speed during the scanning of the spatial region, with the rotation being synchronized to the receipt of signals based on x-ray radiation with the x-ray-sensitive sensor. The rotational or center axis of the device is hereby preferably aligned with the central x-ray beam and/or with the z-axis of the polar coordinate system. Generally the device for influencing the x-ray radiation is arranged specifically in front of an x-ray emitter or x-ray tube. It is however also possible to modify the x-ray emitter or x-ray tube in such a manner that the device for influencing the x-ray radiation is arranged in the x-ray emitter or x-ray tube.

The advantages of the inventive method are that the positions of at least the part of the medical instrument in a plane of an x-ray image are determined automatically by means of a computation facility based on the signals detected with the x-ray-sensitive sensor and can be overlaid for example on an x-ray image obtained using the x-ray facility from the same perspective and that unlike the use of x-ray fluoroscopy images for navigation purposes the x-ray dose to which the patient and in particular the medical personnel are exposed is reduced. Nor is there any need to register coordinate systems, since the determined positions and/or coordinates of the part of the medical instruments are already coordinates of the image coordinate system of the x-ray facility, which can be converted at will from polar coordinates to Cartesian or even other coordinates.

According to variants of the invention the medical instrument is a catheter, an endoscope, a stent or a biopsy needle. Because of its size or the material from which it is made for example, it may not be possible or it may only be possible with difficulty to see the medical instrument per se in an x-ray image. However the instrument can also be an instrument known per se that can be seen in an x-ray image.

The x-ray-sensitive sensor is preferably arranged specifically at the tip or in the region of the tip or in the region of a front component of the medical instrument. According to one variant of the invention the x-ray-sensitive sensor is a microsensor in the form of an x-ray photodiode.

In one embodiment of the invention the device for influencing the x-ray radiation is preferably a disk-shaped shutter that is impermeable to x-ray radiation, which according to one variant of the invention has an essentially rectangular slot of width d, running essentially from the center of the disk or shutter to the edge of the shutter. Alternatively according to one embodiment of the invention the preferably disk-shaped, x-ray-radiation-impermeable shutter can have a number of openings, which are arranged in a radially offset manner in relation to each other. The openings can also be offset in relation to each other in the circumferential direction of the disk-shaped shutter.

According to a further embodiment of the invention the openings can have a different width from each other, when viewed in the circumferential direction, if the openings are for example rectangular or square openings, or a different diameter from each other, if the openings are for example circular openings.

The slot in the shutter or the openings of the shutter which are offset in the radial direction mean that, when the shutter is rotated at constant angular speed, a periodic signal results at the x-ray-sensitive sensor, from which the angle φ of the part of the medical instrument in the plane of the x-ray image can be determined. Starting from a determinable start time $t_0$ related to the periodic rotation of the shutter, it is possible to determine the angle φ of the part of the medical instrument in the plane of the x-ray image based on a time $t_1$, at which x-ray radiation is detected by the x-ray-sensitive sensor and based on the constant period τ of the rotation of the shutter. The angle φ hereby corresponds to the angle φ of the x-ray-sensitive sensor in the plane perpendicular to the central x-ray beam, in which the x-ray-sensitive sensor is located, as well as to the angle φ of the slot in the shutter in the plane of the shutter perpendicular to the central x-ray beam during the detection of x-ray radiation with the x-ray-sensitive sensor.

The angle φ can finally be determined according to the following equation:

$$\varphi = \frac{t_1 - t_0}{\tau} \cdot 2\pi \quad (1)$$

According to one embodiment of the invention the radius R (radial coordinate in polar coordinates) of the part of the medical instrument in the plane of the x-ray image can be determined with the aid of the beam set using the known focal point to detector distance c, the known distance a between the shutter and the focal point of the x-ray beam source and the radius r in polar coordinates on the shutter of the x-ray beam(s) striking the x-ray-sensitive sensor. The focal point to detector distance c and the distance a between the shutter and the focal point of the x-ray beam source are hereby known from the design of the x-ray facility, so that the radius R can be determined according to the following equation $$R = r \cdot \frac{c}{a}. \quad (2)$$

The radius r on the shutter of the x-ray beam(s) striking the x-ray-sensitive sensor can be determined from the slot or opening geometry of the shutter, from which the following applies:

$$r = \frac{d}{2 \cdot \sin\left(\pi \cdot \frac{\Delta t}{\tau}\right)}. \quad (3)$$

d here is the width of the slot or an opening in the shutter, $\Delta t$ is the duration of the signal detected with the x-ray-sensitive sensor and $\tau$ is the period of the rotation of the shutter.

Alternatively in the case of a shutter with radially offset openings, which have a different width or diameter from each other, the radius r on the shutter of the x-ray beams striking the x-ray-sensitive sensor can be determined essentially only from the duration of the signal of the x-ray-sensitive sensor, since the opening geometries or dimensions of the individual openings and the angular speed of the shutter are known. A specific opening geometry and thus a specific radius r correspond here to a specific duration of the signal measured with the x-ray-sensitive sensor. Calibration is recommended in some instances before commissioning of the x-ray facility with this manner of determining the radial component r.

According to another embodiment of the invention the device for influencing the x-ray radiation has a wedge filter. The wedge filter is preferably essentially disk-shaped, with x-ray radiation absorption by the wedge filter decreasing or increasing from radially outside to radially inside or from radially inside to radially outside. X-ray radiation absorption by the wedge filter here is generally a function of the radial coordinate of the wedge filter.

According to a further embodiment of the invention the wedge filter has a preferably thin slot running continuously from inside to outside to generate a signal peak at the x-ray-sensitive sensor so that it is possible to use the signal peak to determine the angle $\phi$ in polar coordinates of the part of the medical instrument in the plane of the x-ray image. At the time of the detection of the signal peak by the x-ray-sensitive sensor due to the x-ray radiation passing through the thin slot of the wedge filter and striking the x-ray sensitive sensor the angle $\phi$ in polar coordinates of the thin slot of the wedge filter in the plane of the wedge filter corresponds, as in the case of the shutter mentioned above, to the angle $\phi$ of the x-ray-sensitive sensor in the plane of the x-ray-sensitive sensor and thus of the part of the medical instruments as well as to the angle $\phi$ of the part of the medical instrument in the plane of the x-ray image. The angle $\phi$ is hereby specified in relation to an angle $\phi_{0K}$, which is associated with a start time $t_{0K}$ related to the periodic rotation of the wedge filter. Thus according to a variant of the invention the angle $\phi$ of the part of the medical instrument in the plane of the x-ray image can be determined starting from the above-mentioned start time $t_{0K}$ related to the periodic rotation of the wedge filter based on a time $t_{1K}$ of detection of the signal peak by the x-ray-sensitive sensor and the constant period $\tau_K$ of the rotation of the wedge filter.

The angle $\phi$ is therefore obtained as follows $$\varphi = \frac{t_{1K} - t_{0K}}{\tau_K} \cdot 2\pi. \quad (4)$$

The radius R in polar coordinates of the part of the medical instrument in a plane of an x-ray image can be determined in turn with the aid of the beam set using the known focal point to detector distance c, the known distance $a_K$ between the wedge filter and the focal point of the x-ray beam source and the radius $r_K$ in polar coordinates on the wedge filter of the x-ray beam(s) striking the x-ray-sensitive sensor. The radius R is therefore obtained as follows $$R = r_K \cdot \frac{c}{a_K}. \quad (5)$$

According to one embodiment of the invention the radius $r_K$ in polar coordinates on the wedge filter of the x-ray beam(s) striking the x-ray-sensitive sensor is determined based on the intensity of the x-ray radiation which is detected by the x-ray-sensitive sensor and is a function of the wedge filter. This is possible, since the functional relationship relating to the absorption of x-ray radiation by the wedge filter as a function of the radial coordinate $r_K$ is generally known. Alternatively the relationship can also be determined in a calibration process, so that the radius $r_K$ in polar coordinates on the wedge filter can be determined based on the measured values from the x-ray-sensitive sensor and on the calibration values. In some instances calibration should be carried out taking into account different tissue types, in order to be able to determine the radius $r_K$ on the wedge filter of the x-ray beam(s) striking the x-ray-sensitive sensor based on the intensity of the x-ray radiation detected by the x-ray-sensitive sensor.

Alternatively the radius $r_K$ on the wedge filter can also be determined from the slot geometry of the wedge filter. This gives $r_K$ as follows according to the equation $$r_K = \frac{d_K}{2 \cdot \sin\left(\pi \cdot \frac{\Delta t}{\tau_K}\right)}, \quad (6)$$

where $d_K$ is the width of the slot of the wedge filter, $\Delta t$ is the duration of the signal detected with the x-ray-sensitive sensor and $\tau_K$ is the period of the rotation of the wedge filter.

According to a further embodiment of the invention the device for influencing the x-ray radiation has a disk with material points that absorb x-ray radiation arranged in a specific pattern. The disk is preferably only x-ray-radiation-permeable at the material points that absorb x-ray radiation. According to one variant of the invention the material points that absorb x-ray radiation have a differing absorption of x-ray radiation. This can be achieved for example in such a manner that the x-ray-radiation-absorbing material, e.g. gold, has differing thicknesses at the different points.

According to one variant of the invention the material points that absorb x-ray radiation are offset radially in relation to each other from the center of the disk or are arranged in a radially offset manner in relation to each other on a spiral coil running from inside to outside. The material points themselves can be circular, rectangular, square or even of some other shape here and can differ from each other in size and/or dimensions. The material points are however arranged in such a manner that there is no gap on the disk when viewed radially.

According to one embodiment of the invention the angle $\phi$ in polar coordinates of the part of the medical instrument in the plane of the x-ray image is determined starting from a start time $t_{0S}$ related to the periodic rotation of the disk based on a time $t_{1S}$ of the detection of x-ray radiation by the x-ray-sensitive sensor and the constant period $\tau_S$ of the rotation of the disk. The angle $\phi$ is therefore obtained as follows $$\varphi = \frac{t_{1S} - t_{0S}}{\tau_S} \cdot 2\pi. \quad (7)$$

In the case of the disk too the radius R in polar coordinates of the part of the medical instrument in the plane of the x-ray image can be determined with the aid of the beam set using the known focal point to detector distance c, the known distance as between the disk and the focal point of the x-ray beam source and the radius $r_S$ in polar coordinates on the disk of the x-ray beam(s) striking the x-ray-sensitive sensor. The radius R is then obtained as follows $$R = r_S \cdot \frac{c}{a_S}. \tag{8}$$

According to one embodiment of the invention the radius $r_S$ on the disk of the x-ray beam(s) striking the x-ray-sensitive sensor is determined based on the intensity of the x-ray radiation, which is detected by the x-ray-sensitive sensor and is a function of the x-ray-absorbing material points. If it is known which material point has what x-ray absorption, it is possible to draw conclusions from the intensity of the x-ray radiation measured with the x-ray-sensitive sensor about the radius $r_S$ on the disk of the x-ray beam(s) stroking the x-ray-sensitive sensor. In some circumstances calibration is also necessary in this instance, in order to be able to take into account the influence of different tissues present during operation and their absorption correspondingly when evaluating the intensities measured with the x-ray-sensitive sensor.

Alternatively the radius $r_S$ on the disk can be determined from the geometry of the material points according to the following equation $$r_S = \frac{d_M}{2 \cdot \sin\left(\pi \cdot \frac{\Delta t}{\tau_S}\right)} \tag{9}$$

where $d_M$ is the width of the material point, $\Delta t$ is the duration of the signal detected with the x-ray-sensitive sensor and $\tau_S$ is the period of the rotation of the disk.

According to a further variant of the invention the disk has a material layer of varying thickness to form material points, with the thickness of the material layer obeying the formula:

$$D \propto \sin(\phi \cdot k \cdot r_S), \tag{10}$$

where D is the thickness of the material layer, $\phi$ is the angle in polar coordinates on the disk of the x-ray beam(s) striking the x-ray-sensitive sensor, $r_S$ is the radius in polar coordinates on the disk of the x-ray beam(s) striking the x-ray-sensitive sensor and k is a suitably selected constant. The material layer is preferably a metal layer, which is arranged on a base layer that is transparent to x-ray radiation. According to one embodiment of the invention a signal is measured at the x-ray-sensitive sensor during rotation of the disk at constant speed, said signal being subjected to a frequency and phase analysis to determine the radius $r_S$ and angle $\phi$. While $\phi$ corresponds to the angle in polar coordinates of the part of the medical instrument in the plane of the x-ray image, the measured frequency corresponds to the product of k and $r_S$, so that $r_S$ can be determined.

According to a further variant of the invention an RFID chip (Radio Frequency Identification Chip) is assigned to the x-ray-sensitive sensor. This allows the signals detected with the x-ray-sensitive sensor to be transmitted wirelessly to a receive station, which is connected to a computation facility.

According to a further variant of the invention the x-ray-sensitive sensor is also supplied wirelessly with energy by way of the RFID chip. The RFID chip is hereby supplied wirelessly with energy by way of an inductive or capacitive coupling and makes some of the energy provided available to the x-ray-sensitive sensor for the latter's operation.

According to variants of the invention the x-ray facility is a monoplane x-ray facility or a biplane x-ray facility, which make it possible to determine not only the position of at least a part of the medical instrument in the plane of an x-ray image but also the position of at least the part of the medical instrument provided with at least one x-ray-sensitive sensor in space, based on two scans carried out at different angles by means of triangulation. As with conventional monoplane or biplane x-ray units, with which it is possible to determine the spatial position of an instrument recorded in the x-ray projection recordings from two x-ray projections recorded at different projection angles with knowledge of the projection geometries of the monoplane or biplane x-ray facility, this is also possible in the case of the present invention based on two scans carried out at different angles.

The object relating to the device is achieved by a device having a monoplane x-ray facility or a biplane x-ray facility with at least one x-ray beam source, to which at least one device influencing the x-ray radiation emitted by the x-ray beam source is specifically assigned, at least one x-ray-sensitive sensor to be arranged on a medical instrument and having a computation facility, which is set up to carry out one of the methods described above.

BRIEF DESCRIPTION OF THE DRAWINGS

Exemplary embodiments of the invention are illustrated in the accompanying drawings, in which.

DETAILED DESCRIPTION OF THE INVENTION

Figure 1:
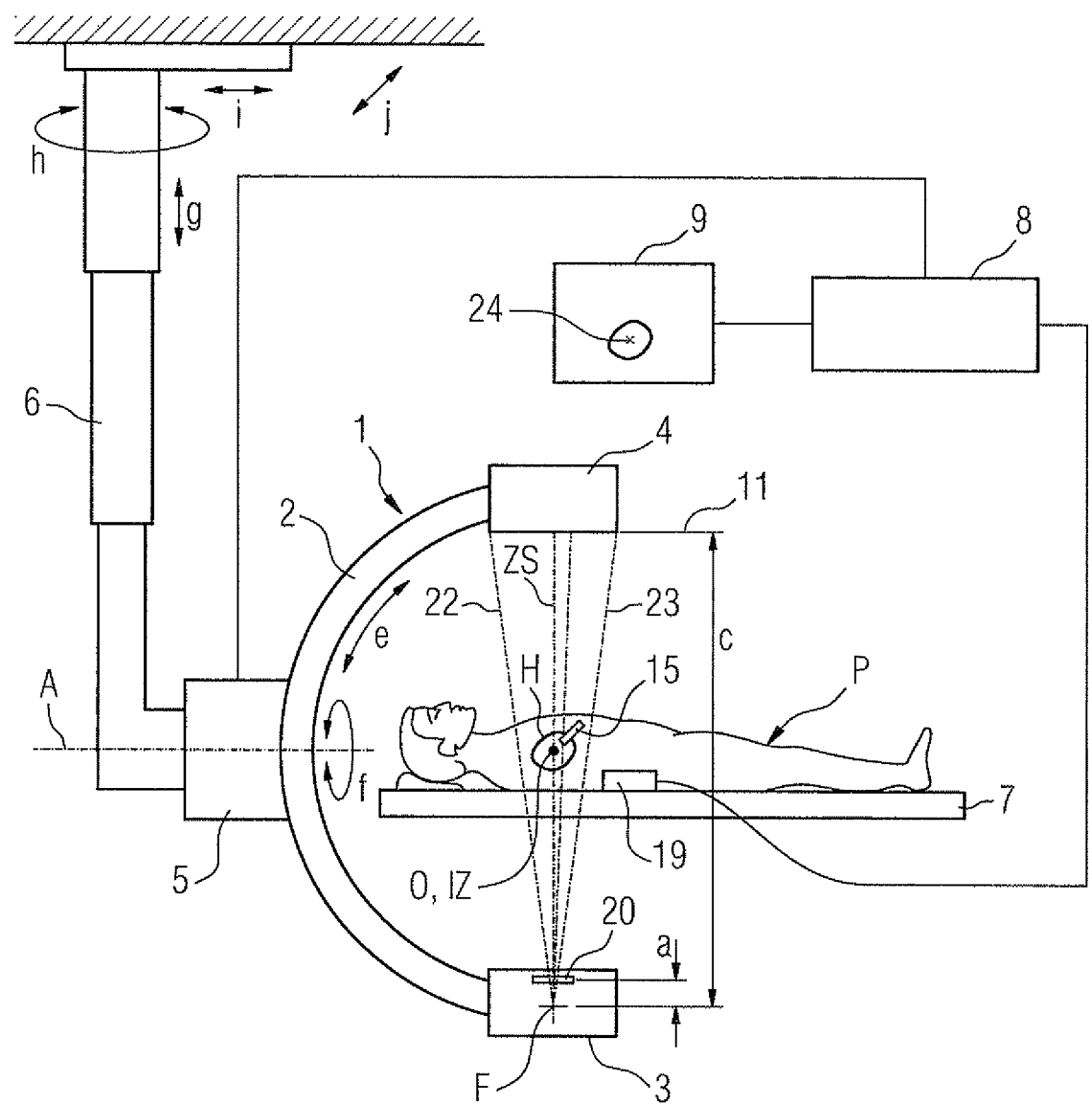
FIG. 1 shows an x-ray facility for carrying out the inventive method.

FIG. 1 shows an inventive device with a monoplane x-ray facility in the form of a C-arm x-ray device 1. The C-arm x-ray device 1 has a C-arm 2, on which an x-ray beam source 3 and an x-ray beam detector 4 are arranged opposite each other. A central beam ZS of an x-ray beam bundle emitted from the x-ray beam source 3 hereby passes at least essentially through the isocenter IZ of the C-arm 2 striking the input window of the x-ray beam receiver 4 at least approximately in the center. The C-arm 2 is mounted on a support 5 in such a manner that it can be adjusted about its orbital axis O in the directions of the double arrow e. In the present exemplary embodiment the support 5 is arranged on a ceiling gantry 6, offering the adjustment options marked with double arrows g, h, i and j in FIG. 1 for the support 5 provided with the C-arm 2. The support 5 and C-arm 2 can also be pivoted about the angulation axis A in the direction of the double arrow f.

It is possible to obtain 2D x-ray images and 3D images of an object in the manner known per se using the C-arm x-ray device 1. In the present exemplary embodiment the object is a patient P supported on a schematically illustrated patient table 7. Generally the patient table 7 with the patient P and the C-arm 2 of the C-arm x-ray device 1 are aligned in relation to each other in such a manner that a tissue region of the patient P that is of interest and is to be shown in an x-ray image comes to be located at least essentially in the isocenter IZ of the C-arm 2. To operate the C-arm x-ray device 1 a computation facility 8 is provided, which also serves for image processing. 2D or 3D images recorded with the C-arm x-ray device 1 can be displayed on a display device 9.

Figure 2:
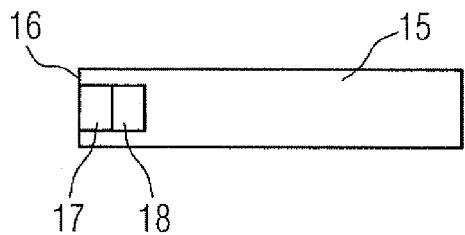
FIG. 2 shows an enlarged diagram of a catheter.

In the present exemplary embodiment the C-arm x-ray device 1 is provided to assist with a medical intervention on the heart H of the patient P. During the medical intervention a catheter 15 has to be navigated in relation to the heart H and/or in the heart H of the patient P. During navigation of the catheter 15 with the aid of the C-arm x-ray device 1 the patient P and the medical personnel carrying out the navigation should be exposed to as little x-ray radiation as possible. In order to be able to achieve this, in the present exemplary embodiment, the catheter 15, shown enlarged in FIG. 2, is provided at its tip 16 with an x-ray-sensitive sensor, in the present exemplary embodiment an x-ray photodiode 17, which can be used to detect x-ray radiation. In the present exemplary embodiment the x-ray photodiode 17 is assigned an RFID chip 18, to which the x-ray photodiode 17 is connected electrically. The RFID chip 18 can be used to transmit the signals detected with the x-ray photodiode 17 and based on x-ray radiation wirelessly to a receive unit 19, which in the present exemplary embodiment is arranged on the patient table 7. The receive unit 19 is connected to the computation facility 8, so that the signals detected with the x-ray photodiode 17 are available to the computation facility 8 of the C-arm x-ray device 1 for further analysis and processing. The RFID chip 18 is also supplied wirelessly with energy by the receive unit 19 by means of a capacitive or inductive coupling, said energy also being used to operate the x-ray photodiode 17. This means there is no need for electrical connecting cables for energy transmission to the x-ray photodiode 17 and for signal transmission from the x-ray photodiode 17 to the computation facility 8.

In the present exemplary embodiment a shutter 20 for influencing the x-ray radiation emitted from a focal point F of the x-ray beam source 3 is assigned specifically to the x-ray beam source 3, which means among other things that the shutter 20 is arranged at a known distance a from the focal point F of the x-ray beam source 3. In the present exemplary embodiment the shutter 20 is arranged in the housing of the x-ray beam source 3. Generally but not necessarily the shutter 20 is arranged in front of the beam exit window of the x-ray emitter having an x-ray tube. The shutter 20 can however also be arranged at another point, for example in the x-ray emitter, to influence the x-ray radiation emitted from a focal point F. The shutter 20 can also be removed from the beam path in a manner not shown in the figures, in order to be able to obtain x-ray images of the patient in the conventional manner.

Figure 3:
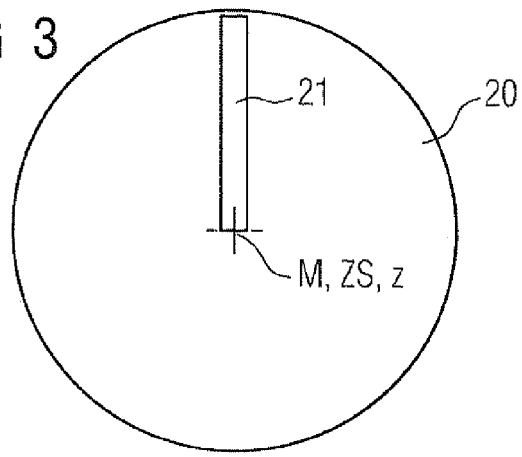
FIG. 3 shows a shutter with a slot.

As shown in FIGS. 1 and 3, the shutter 20 is configured essentially as a circular disk and is impermeable to x-ray radiation apart from a slot 21. The shutter can be rotated about its center axis M by drive means (not shown in the figures), its center axis M being aligned at least essentially with the central beam ZS of an x-ray beam bundle emitted from the focal point F of the x-ray beam source 3 and a z-axis of a polar coordinate system.

In the process of assisting with the navigation of the catheter 15 with the aid of the C-arm x-ray device 1, periodic rotation of the shutter 20 at constant angular speed about its center axis M makes it possible to scan the spatial region 22, in which navigation is being carried out with the catheter 15 provided with the x-ray photodiode 17, periodically with x-ray radiation emitted from the focal point F of the x-ray beam source 3, with x-ray radiation only being able to travel in the direction of the patient P and the x-ray beam receiver 4 through the slot 21 in the shutter 20, so that both the patient P and the personnel carrying out the navigation operation are exposed to a smaller x-ray dose during navigation. The scanned spatial region 22 is essentially conical due to a further shutter of the x-ray beam source 3 (not shown in detail in the figures). With each rotation of the shutter 20 the entire spatial region 22 is scanned with x-ray radiation. Whenever x-ray beams passing through the slot 21 strike the x-ray photodiode 17, a signal is detected at the x-ray photodiode 17. Such an x-ray beam, 23 is shown in FIG. 1. Based on the x-ray radiation detected with the x-ray photodiode 17 it is now possible to determine the position of the x-ray photodiode 17, which is arranged specifically at the tip 16 of the catheter 15, and thus the tip 16 of the catheter 15 in the plane 11 of an x-ray image, which corresponds essentially to the plane of the input window of the x-ray beam receiver 4, and thus to overlay it on a 2D x-ray image from the same perspective or spatial direction.

Figure 4:
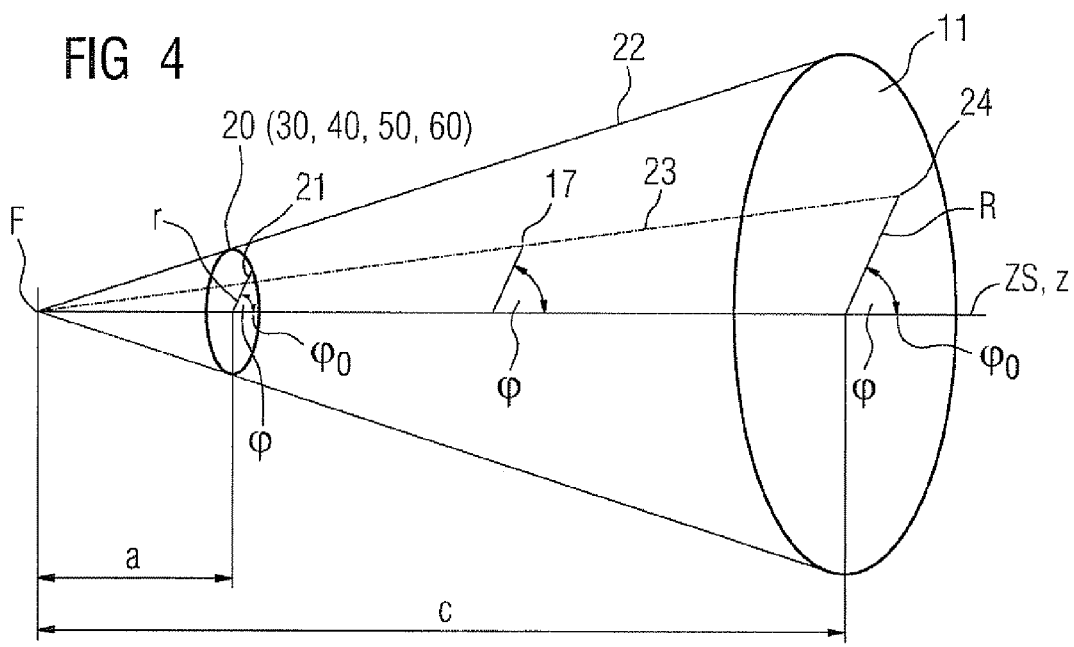
FIG. 4 shows an illustration of the geometric imaging conditions of the x-ray facility from FIG. 1, FIG. 5 a schematic illustration of a signal diagram of the x-ray-sensitive sensor.

FIG. 4 shows the geometric imaging conditions of the C-arm x-ray device 1 again in a different perspective. The coordinates of the tip 16 of the catheter 15 in the plane 11 of the x-ray image associated with the position 24 are determined based on the geometric conditions in polar coordinates, with the z-axis, as already mentioned, being aligned with the central beam ZS of the of the x-ray beam bundle emitted from the focal point F of the x-ray beam source 3. The structural conditions of the C-arm x-ray device 1 mean that the focal point to detector distance c and the distance a between the shutter 20 and the focal point F are known.

If, as shown in FIG. 4, the x-ray beam 23 passes through the slot 21 in the shutter 20 and strikes the x-ray photodiode 17, the angle φ in the plane 11 of the x-ray image corresponds to the angle φ on the shutter 20, which is arranged in a plane perpendicular to the central beam ZS. The further the x-ray photodiode 17 is away from the axis of rotation (z-axis), the shorter the time, in which the x-ray photodiode 17 detects x-ray radiation. The time until x-ray radiation strikes the x-ray photodiode 17 is approximately reciprocal to the distance between the x-ray photodiode 17 and the central beam ZS.

Figure 5:
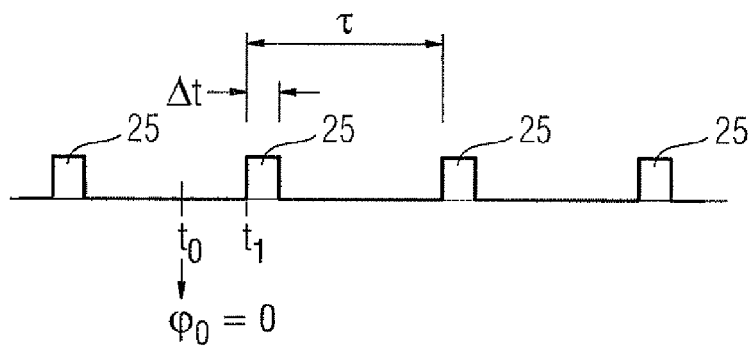

FIG. 5 shows the signals 25 plotted over time, as obtained with the x-ray photodiode 17 during rotation of the shutter 20 at constant angular speed. Based on these signals it is possible to calculate the angle φ according to the equation (1):

$$\varphi = \frac{t_1 - t_0}{\tau} \cdot 2\pi, \tag{1}$$

where φ is the angle of the tip 16 of the catheter 15 in the plane 11 of the x-ray image, $t_0$ is the start time related to the periodic rotation of the shutter 20, at which φ=0°, $t_1$ is the time of the detection of x-ray radiation by the x-ray photodiode 17 and τ is the period of the rotation of the shutter 20.

Figure 6:
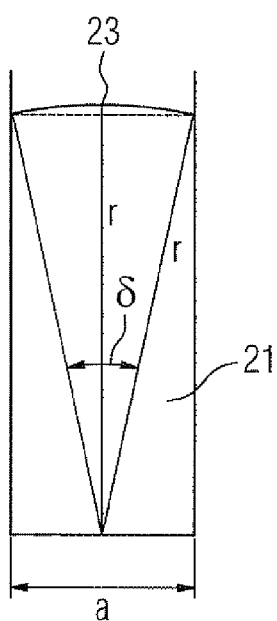
FIG. 6 shows an illustration of the geometric conditions of the slot in the shutter from FIG. 3.

The radius R of the tip 16 of the catheter 15 in the plane 11 of the x-ray image can be determined with the aid of the beam set using the known focal point to detector distance c, the known distance a between the shutter 20 and the focal point F of the x-ray beam source 3 and the radius r in polar coordinates on the shutter 20 of the x-ray beam 23 striking the x-ray photodiode 17. The radius r on the shutter 20 can be obtained here among other things from the slot geometry of the slot 21, as shown in FIG. 6. According to this, the following applies:

$$\sin\frac{\delta}{2} = \frac{d}{2r};$$

from which:

$$\delta = 2\arcsin\frac{d}{2r}$$

The following also applies:

$$\frac{\Delta t}{\tau} = \frac{\delta}{2\pi} = \frac{1}{\pi}\arcsin\frac{d}{2r}$$

This gives $$r = \frac{d}{2\cdot\sin\left(\pi\frac{\Delta t}{\tau}\right)}.$$

With Δt<<τ the following applies:

$$r = \frac{d\cdot\tau}{2\pi\cdot\Delta t}.$$

It is thus possible to determine R with the beam set as follows:

$$R = r\cdot\left(\frac{c}{a}\right), \quad (2)$$

where R is the radius or the radial coordinate of the tip 16 of the catheter 15 in the plane 11 of the x-ray image, r is the radius or the radial coordinate on the shutter 20 of the x-ray beam 23 striking the x-ray photodiode 17, c is the known focal point to detector distance and a is the known distance between the shutter 20 and the focal point F of the x-ray beam source 3.

It is thus possible, based on the x-ray radiation detected with the x-ray photodiode 17, in particular based on the signals 25, to determine the position of at least the tip 16 of the catheter 15 in the plane 11 of an x-ray image. Determination of the coordinates associated with the position 24 is carried out here by the computation facility 8, which is operated with a corresponding computer program and to which the signals required for the determination on the part of the x-ray photodiode 17 are made available. It is thus possible to overlay the position of at least the tip 16 of the catheter 15 on an x-ray image obtained using the C-arm x-ray device 1, in particular to assist with the navigation of the catheter 15, even if the material selection or miniaturization of the catheter 15 means that the x-ray photodiode 17 and RFID chip are not x-ray-positive and would thus not be imaged in an x-ray image.

Figure 7:
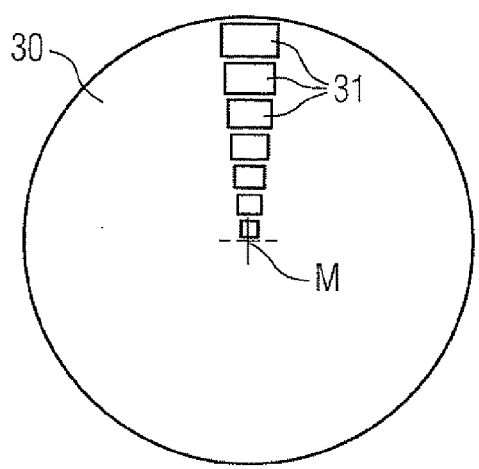
FIG. 7 shows a shutter with a number of openings.

As an alternative to the shutter 20 the shutter 30 shown in FIG. 7 could also be used, being similarly impermeable to x-ray radiation apart from openings 31. The shutter 30 is similarly in the shape of a circular disk, with the openings 31 increasing in width from inside to outside. Depending on which of the openings x-ray beams pass through, x-ray beams are detected with the x-ray photodiode 17 for a shorter or longer time, so that after corresponding calibration it is possible to draw conclusions about the radius r on the shutter 30 of the x-ray beam(s) striking the x-ray photodiode 17, based on the duration of a signal detected with the x-ray photodiode 17. The shutter 30 will generally have more openings 31 than are shown in FIG. 7. The openings 31 can also be arranged with an offset in the circumferential direction.

Figure 8:
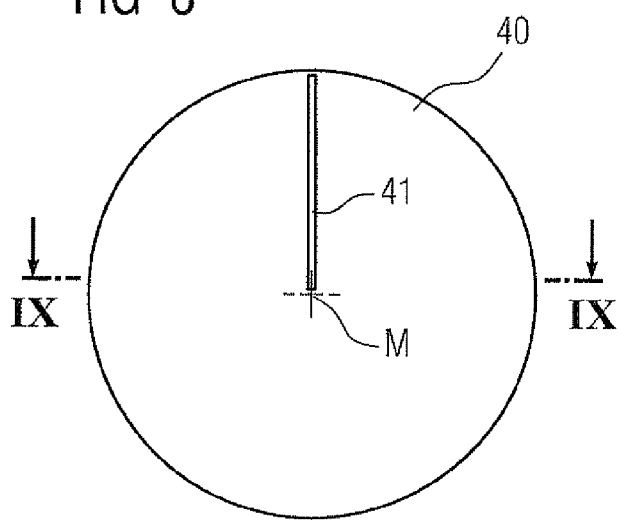
FIG. 8 shows a top view of a wedge filter.
Figure 9:
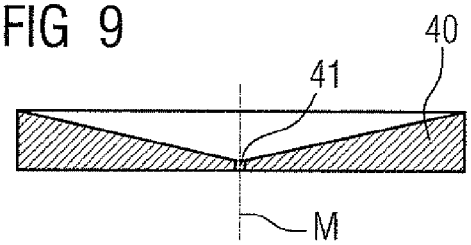
FIG. 9 shows the view of the section IX of the wedge filter from FIG. 8.

A further alternative to the shutter 20 is the wedge filter 40 shown in a top view in FIG. 8, its sectional view being shown in FIG. 9. In the present embodiment the wedge filter 40 is configured in such a manner that it has less x-ray radiation absorption in the region of the axis of rotation or the center axis M than at the periphery. Starting from the center axis M x-ray radiation absorption therefore increases radially outward. The wedge filter 40 also has a thin slot 41 to generate a signal peak at the x-ray photodiode 17, based on which the angle φ of the tip 16 of the catheter 15 in the plane 11 of the x-ray image can be determined. The angle φ is determined here in the manner described above, i.e. the angle φ is obtained as follows $$\varphi = \frac{t_{1K} - t_{0K}}{\tau_K}\cdot 2\pi, \quad (4)$$

where φ is the angle of the tip 16 of the catheter 15 in the plane 11 of the x-ray image, $t_{0K}$ is the start time related to the periodic rotation of the wedge filter 40, $t_{1K}$ is the time of the detection of the signal peak by the x-ray photodiode 17 and $\tau_K$ is the period of the rotation of the wedge filter 40.

For the wedge filter 40 too it is also possible to determine the radius R of the tip 16 of the catheter 15 in the plane 11 of the x-ray image with the aid of the beam set using the known focal point to detector distance c, the known distance $a_K$ between the wedge filter and the focal point F of the x-ray beam source 3 and the radius $r_K$ in polar coordinates on the wedge filter 40 of the x-ray beam 23 striking the x-ray photodiode 17. The radius $r_K$ on the wedge filter 40 of the x-ray beam 23 striking the x-ray photodiode 17 is hereby determined based on the intensity of the x-ray radiation which is detected by the x-ray photodiode 17 and is a function of the wedge filter. This is possible, because the absorption characteristics of the wedge filter 40 or the absorption of the wedge filter 40 as a function of the radial component is known. In some instance calibration can also be carried out, in order to be able to draw conclusions from the intensity of the x-ray radiation detected with the x-ray photodiode 17 about the radial component $r_K$ on the wedge filter 40 of the x-ray beam 23 striking the x-ray photodiode 17.

Figure 10:
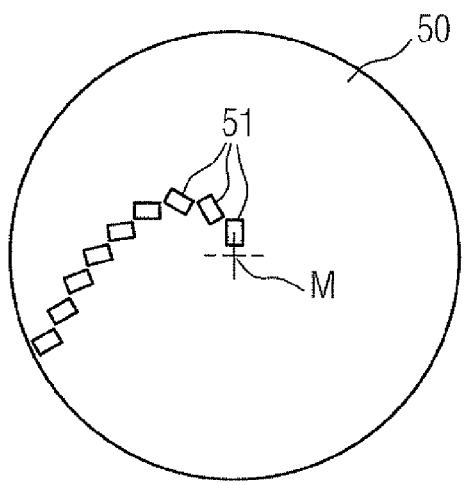
FIG. 10 shows a disk with x-ray-absorbing material points arranged in a specific pattern and FIG. 11 shows a disk having a material layer with spatially varying thickness.

As a further alternative to the shutter 20, the disk 50 shown in FIG. 10 can be used, being provided with material points 51 that absorb x-ray beams and are arranged in a specific pattern. The disk 50 is impermeable to x-ray radiation apart from the material points 51 that absorb x-ray rays. In the present exemplary embodiment the material points 51, which have a differing absorption of x-ray radiation, are arranged essentially from the center of the disk out on a spiral coil running from inside to outside. As described above, in the case of the disk 50 the angle φ can also be determined based on the signals 25 detected with the x-ray photodiode 17. The angle φ is then obtained as follows $$\varphi = \frac{t_{1S} - t_{0S}}{\tau_S} \cdot 2\pi, \qquad (7)$$

where φ is the angle of the tip 16 of the catheter 15 in the plane 11 of the x-ray image, $t_{0S}$ is the start time related to the periodic rotation of the disk 50, $t_{1S}$ is the time of the detection of x-ray radiation by the x-ray photodiode 17 and TS is the period of the rotation of the disk 50.

The radius R of the tip 16 of the catheter 15 in the plane 11 of the x-ray image is in turn obtained using the beam set, according to which $$R = r_S \cdot \frac{c}{a_S}, \qquad (8)$$

where R is the radius of the tip 16 of the catheter 15 in the plane 11 of the x-ray image, $r_S$ is the radius on the disk 50 of the x-ray beam 23 striking the x-ray photodiode 17, c is the known focal point to detector distance and $a_S$ is the known distance between the disk 50 and the focal point F of the x-ray beam source 3. The radius $r_S$ on the disk 50 is hereby obtained based on the intensity of the x-ray radiation which is detected by the x-ray photodiode 17 and is a function of the material points 51 that absorb x-ray beams. The known absorption characteristics of the material points 51 mean that it is possible to ascertain the radius $r_S$ on the disk 50.

The radius $r_S$ on the disk 50 can however also be determined from the pattern point geometry, according to which $$r_S = \frac{d_M}{2 \cdot \sin\left(\pi \cdot \frac{\Delta t}{\tau_S}\right)}, \qquad (9)$$

where $d_M$ is the width of the pattern point, Δt is the duration of the signal detected with the x-ray photodiode 17 and $\tau_S$ is the period of the rotation of the disk 50.

Figure 11:
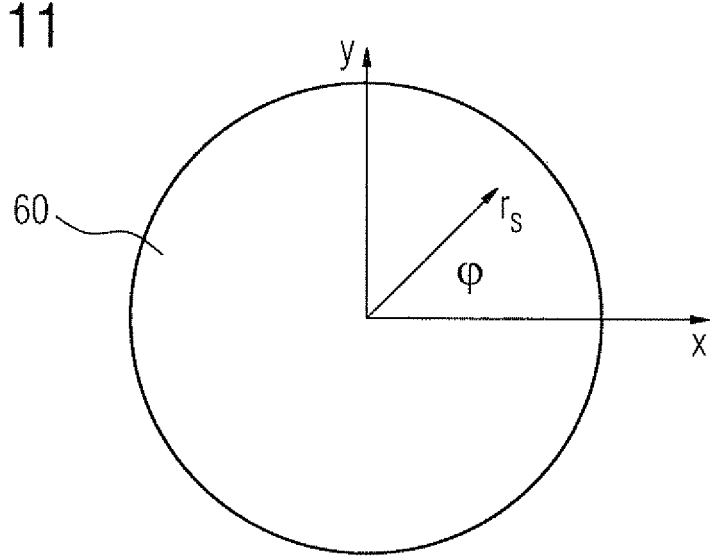
Figure 12:
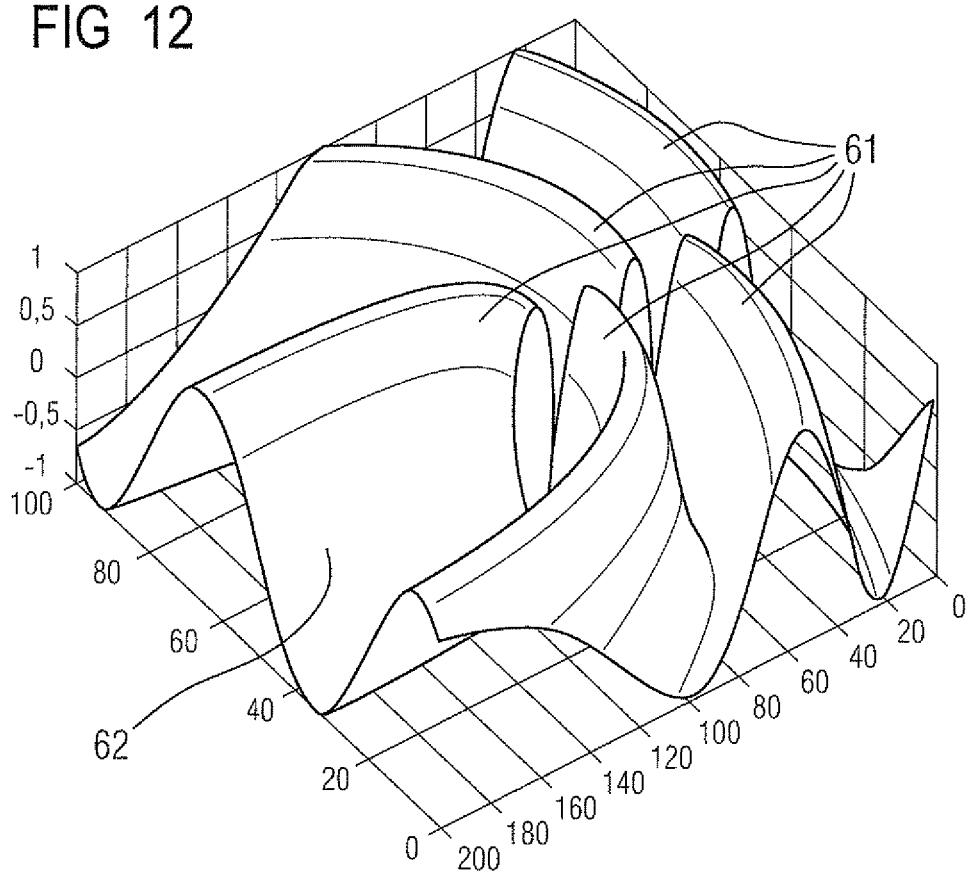
FIG. 12 shows a schematic illustration of a material layer from FIG. 11 with an exemplary embodiment of k=5.

FIG. 11 shows a schematic diagram of a further alternative to the shutter 20. This is a disk 60. The disk 60 is assigned a polar coordinate system and a Cartesian coordinate system in the same manner as the shutter 20 (see also FIG. 4). As shown schematically in the Cartesian coordinate system for the purposes of illustration in FIG. 12, the disk 60 has a specific pattern of material points that absorb x-ray radiation. The material points result from the spatially varying thickness of a material layer. The thickness of the material layer here obeys the formula $$D \propto \sin(\varphi \cdot k \cdot r_S), \qquad (10)$$

where D is the thickness of the material layer, φ is the angle in polar coordinates on the disk 60, $r_S$ is the radius in polar coordinates on the disk 60 and k is a selected constant. FIG. 12 shows an exemplary embodiment of k=5. In the present exemplary embodiment the disk 60 has a metal layer 62 with spatially varying thickness, which is applied to a base layer that is transparent to x-ray beams. As mentioned above, the thickness of the metal layer 62 obeys the formula (10), with the result that five material points of maximum thickness 61 are formed in the present exemplary embodiment.

During rotation of the disk 60 at constant speed a signal is measured with the x-ray photodiode 17, said signal being subjected to a frequency and phase analysis to determine the radius $r_S$ in polar coordinates on the disk 60 of the x-ray beam(s) striking the x-ray photodiode 17 and the angle φ in polar coordinates on the disk 60 of the x-ray beam(s) striking the x-ray photodiode 17. The angle φ in polar coordinates of the tip 16 of the catheter 15 in the plane 11 of the x-ray image, which corresponds to the angle φ on the disk 60, can be determined as described above starting from a specific start time $t_{0S}$ related to the periodic rotation of the disk 60 based on a time $t_{1S}$ of the detection of x-ray radiation of a specific intensity by the x-ray photodiode 17 and the constant period $\tau_S$ of the rotation of the disk 60 using the equation $$\varphi = \frac{t_{1S} - t_{0S}}{\tau_S} \cdot 2\pi. \qquad (7)$$

This is possible because the absorption pattern or absorption response of the disk 60 is known.

The frequency ($1/\tau_S$) measured with the x-ray photodiode 17 corresponds to the product of k and $r_S$, so that $r_S$ can be determined.

$r_S$ could also be determined by storing the absorption patterns that are a function of $r_S$ in the computer 8 during a calibration process and determining $r_S$ based on a measured absorption pattern.

The radius R of the tip 16 of the catheter 15 in the plane 11 of the x-ray image is in turn obtained from the equation $$R = r_S \cdot \frac{c}{a_S}. \qquad (8)$$

It is becoming clear therefore that the method described above can be used to overlay the position of at least the tip 16 of the catheter 15 on an x-ray image, for example for navigation purposes, automatically and with a reduction of the x-ray dose to which the patient and medical personnel are exposed.

If medical personnel are also interested in the position of the tip 16 of the catheter 15 in space, the C-arm 2 is pivoted about its orbital axis or about its angulation axis, to scan the spatial region at a different angle. Based on the positions of the tip 16 of the catheter 15, which were determined at two differing but known angles, it is possible to determine the coordinates of the tip 16 of the catheter 15 in space taking into account the known projection geometries by means of triangulation.

In the present exemplary embodiment the device comprises a monoplane x-ray facility. The device can however also comprise a biplane x-ray facility, so that it is possible in particular to determine the coordinates of the tip 16 of the catheter 15 in space without adjusting a C-arm, since it is possible to scan a spatial region with both C-arms of the biplane x-ray facility.

In contrast to the exemplary embodiment described above, the medical instrument does not necessarily have to be a catheter. Rather the medical instrument, which is inserted into the body of a patient, can also be an endoscope, a stent, a biopsy needle or another instrument to be navigated or made visible.

It is also possible to arrange a number of x-ray-sensitive sensors, in other words a number of x-ray photodiodes 17, on the instrument, in order also to be able to obtain directional information from the medical instrument.

The shutter 30, the wedge filter 40 and the disk 50 can also be removed from the beam path of the x-ray radiation.

Also the rotation axis of the device for influencing the x-ray radiation does not necessarily have to be aligned with the central beam ZS of the x-ray radiation.

The device for influencing the x-ray radiation can also be configured in a different manner from the one described above, in so far as the device for influencing the x-ray radiation ensures that x-ray radiation of a similar spatial and temporal form is emitted, as for example with the aid of the shutter 20.

In contrast to the exemplary embodiment described above, the x-ray facility can also be an x-ray computed tomograph.

The invention claimed is:

1. A method for determining a position of a part of a medical instrument provided with an x-ray sensitive sensor in a plane of an x-ray image using an x-ray device, comprising:
    mechanically scanning by way of a shutter a spatial region in which the medical instrument provided with the x-ray sensitive sensor is located by x-ray radiation emitted from an x-ray beam source of the x-ray device;
    arranging an x-ray beam detector opposite and spaced-apart from the x-ray beam source, wherein the medical instrument with the x-ray sensitive sensor is interposed between the x-ray beam source and the x-ray beam detector;
    while x-ray radiation is emitted by the x-ray beam source, rotating at a constant speed the shutter which is coupled to the x-ray beam source for influencing the x-ray radiation emitted by the x-ray beam source, the shutter having a central axis and wherein said rotating is performed about the central axis of the shutter;
    detecting the x-ray radiation by the x-ray sensitive sensor;
    synchronizing the rotation of the shutter to the detection of the x-ray radiation by the x-ray sensitive sensor;
    automatically determining the position of the part of the medical instrument in the plane of the x-ray image based on the following:

$$\varphi = \frac{t_1 - t_0}{\tau} \cdot 2\pi,$$

where $\varphi$ represents an angle of tip of the medical instrument in the plane of the x-ray image, $t_0$ represents an initial time regarding a constant rotation of the shutter, $t_1$ represents a time at which x-ray radiation is detected by the x-ray sensitive sensor, and $\tau$ represents a period of the constant rotation of the shutter;

$$R = \frac{c}{a} \cdot r,$$

wherein R represents radius of the tip of the medical instrument in the plane of the x-ray image, r represents radius on the shutter of the x-ray beam striking the x-ray sensitive sensor, c represents a distance from a focal point of the-ray beam to the x-ray beam detector, and a represents a distance from the focal point of the-ray beam to the shutter; and
wherein the medical instrument is inserted into a body of a patient; and overlaying the position of the tip of the medical instrument on the x-ray image for assisting navigation of the medical instrument without registration even if the medical instrument and the x-ray sensitive sensor can not be seen or is difficult to be seen in the x-ray image because of material selection or miniaturization of the medical instrument.

2. The method as claimed in claim 1, wherein the medical instrument is selected from a group consisting of: a catheter, an endoscope, a stent, and a biopsy needle.

3. The method as claimed in claim 1, wherein the x-ray sensitive sensor is an x-ray photodiode and arranged at the tip or in a region of the tip or in a region of a front component of the medical instrument.

4. The method as claimed in claim 1, wherein the x-ray device is a monoplane x-ray device or a biplane x-ray device.

5. The method as claimed in claim 1, wherein the position of the part of the medical instrument is determined based on two scans at different angles by triangulation.

6. An imaging device for determining a position of a part of a medical instrument during a medical procedure, comprising:
    an x-ray device that records an x-ray image;
    an x-ray beam source arranged on the x-ray device that emits x-ray radiation for the recording;
    an x-ray beam detector arranged opposite and spaced-apart from the x-ray beam source, wherein the medical instrument is interposed between the x-ray beam source and the x-ray beam detector;
    a shutter coupled to the x-ray beam source to rotatingly scan a spatial region in which the medical instrument is located, wherein the shutter is configured as a disk and, while x-ray radiation is emitted by the x-ray beam source, the shutter is rotated at a constant speed to influence the x-ray radiation emitted by the x-ray beam source, wherein the disk has a central axis and disk rotation is arranged about the central axis of the disk;
    an x-ray sensitive sensor arranged on the medical instrument in a plane of the x-ray image that detects the x-ray radiation; and
    a computation device that automatically:
        determines the position of the part of the medical instrument in the plane of the x-ray image based on the following:

$$\varphi = \frac{t_1 - t_0}{\tau} \cdot 2\pi,$$

where $\varphi$ represents an angle of tip of the medical instrument in the plane of the x-ray image, $t_0$ represents an initial time regarding a constant rotation of the shutter, $t_1$ represents a time at which x-ray radiation is detected by the x-ray sensitive sensor, and $\tau$ represents a period of the constant rotation of the shutter, $$R = \frac{c}{a} \cdot r,$$

wherein R represents radius of the tip of the medical instrument in the plane of the x-ray image, r represents radius on the shutter of the x-ray beam striking the x-ray sensitive sensor, c represents a distance from a focal point of the-ray beam to the x-ray beam detector, and a represents a distance from the focal point of the-ray beam to the shutter; and wherein the medical instrument is inserted into a body of a patient; and overlays the position of the tip of the medical instrument on the x-ray image for assisting navigation of the medical instrument without registration even if the medical instrument and the x-ray sensitive sensor can not be seen or is difficult to be seen in the x-ray image because of material selection or miniaturization of the medical instrument.

7. The device as claimed in claim 6, wherein the shutter has a rectangular slot.

8. The device as claimed in claim 6, wherein the shutter has a number of openings that are arranged radially offset in relation to each other and have a different width or diameter from each other when viewed in a circumferential direction.

9. The device as claimed in claim 6, wherein an angle in a polar coordinate of the part of the medical instrument in the plane of the x-ray image is determined from a start time related to the rotation of the shutter to a time of the detection of the x-ray radiation by the x-ray sensitive sensor and a constant period of the rotation of the shutter.

10. The device as claimed in claim 6, wherein a radius in a polar coordinate of the part of the medical instrument in the plane of the x-ray image is determined based on a distance from a focal point of the x-ray beam source to the x-ray beam detector of the x-ray device, a distance from the focal point to the shutter, and a radius on the shutter of the x-ray radiation striking the x-ray sensitive sensor.

11. The device as claimed in claim 10, wherein the radius on the shutter of the x-ray radiation striking the x-ray sensitive sensor is determined based on a geometry of a slot in the shutter or a number of openings in the shutter and a duration of the detection of the x-ray radiation by the x-ray sensitive sensor.

12. The device as claimed in claim 6, wherein an RFID chip is further arranged on the medical instrument and is electrically coupled to the x-ray sensitive sensor to wirelessly transmit a signal indicative of the x-ray radiation detected by the x-ray sensitive sensor and supply energy to electrically power the x-ray sensitive sensor.

\* \* \* \* \*